(12) United States Patent
Windmiller (10) Patent No.: US 10,492,708 B1
(45) Date of Patent: Dec. 3, 2019

(54) TISSUE-PENETRATING ELECTROCHEMICAL SENSOR FEATURING A CO-ELECTRODEPOSITED THIN FILM COMPRISED OF POLYMER AND BIO-RECOGNITION ELEMENT

(71) Applicant: Biolinq, Inc., San Diego, CA (US)

(72) Inventor: Joshua Windmiller, Del Mar, CA (US)

(73) Assignee: Biolinq, Inc., San Diego, CA (US)

( * ) Notice: Subject to any disclaimer, the term of this patent is extended or adjusted under 35 U.S.C. 154(b) by 0 days.

(21) Appl. No.: 16/152,372

(22) Filed: Oct. 4, 2018

Related U.S. Application Data

(63) Continuation of application No. 15/590,105, filed on May 9, 2017, now Pat. No. 10,092,207.

(60) Provisional application No. 62/336,724, filed on May 15, 2016.

(51) Int. Cl.
| | |
|---|---|
| *A61B 5/05* | (2006.01) |
| *A61M 5/172* | (2006.01) |
| *A61N 1/30* | (2006.01) |
| *A61B 5/145* | (2006.01) |
| *A61N 1/05* | (2006.01) |

(52) U.S. Cl.
CPC ............ *A61B 5/05* (2013.01); *A61B 5/14546* (2013.01); *A61M 5/1723* (2013.01); *A61N 1/05* (2013.01); *A61N 1/30* (2013.01)

(58) Field of Classification Search
CPC ............ A61B 5/14532; A61B 5/14865; A61B 5/14503
See application file for complete search history.

(56) References Cited

U.S. PATENT DOCUMENTS

| | | | |
|---|---|---|---|
| 2003/0104119 A1* | 6/2003 | Wilson ................... | C12Q 1/001 427/2.1 |
| 2011/0087315 A1* | 4/2011 | Richardson-Burns ...................... | A61B 5/0408 607/116 |

* cited by examiner

*Primary Examiner* — Olatunji A Godo
(74) *Attorney, Agent, or Firm* — Clause Eight IPS; Michael Catania (57) ABSTRACT

A method and device to impart the ability to selectively quantify chemical/biochemical analytes occupying physiological fluids via an automated process that allow the precise and spatially-defined simultaneous deposition of a thin-film of polymer containing an immobilized biorecognition element dispersed therein. A tissue penetrating electrochemical sensor comprises at least one working electrode and at least one of a reference electrode and a counter electrode.

14 Claims, 8 Drawing Sheets

TISSUE-PENETRATING ELECTROCHEMICAL SENSOR FEATURING A CO-ELECTRODEPOSITED THIN FILM COMPRISED OF POLYMER AND BIO-RECOGNITION ELEMENT

CROSS REFERENCE TO RELATED APPLICATION

The Present Application is a continuation application of U.S. patent application Ser. No. 15/590,105, filed on May 9, 2017, which claims priority to U.S. Provisional Patent Application No. 62/336,724, filed on May 15, 2016, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to electrochemical sensors.

Description of the Related Art

Electrochemical sensor devices have witnessed increased development activity in recent years, driven primarily by the challenge of in vivo glucose sensing. However, to date, these devices are manufactured using labor- and time-consuming physical assembly processes, especially to impart their selective chemical sensing capabilities. In this vein, such devices have not leveraged high-volume automated manufacturing processes to fabricate electrochemical sensors with high yield and uniformity.

The prior art discusses various sensors.

Meyer et al., U.S. Pat. No. 4,756,807 for a Chemically modified electrodes for the catalytic reduction of CO2 discloses an electrode that has a film adsorbed to its surface by reductive electropolymerization of (vbpy)Re(CO)3 Cl (4-vinyl-4'-methyl-2,2'-bipyridine tricarbonylchlororhenium(I)) or its acetonitrile analogue, [(vbpy)Re(CO)3 (MeCN)]+(4-vinyl-4'-methyl-2,2'-bipyridine tricarbonylacetonitrile rhenium (I)). The poly(vbpy)Re(CO)3 Cl or poly [(vbpy)Re(CO)3 (MeCN)]+adsorbed onto the electrode, acts as a catalyst for CO2 reduction to CO. Stability and the reactivity of the polymer film may be increased by co-reductive electropolymerization of either of the aforesaid Re complexes with [(bpy)2 Ru(vpy)2 2+(bis(4-vinyl-pyridine) bis(2,2'-bipyridine) ruthenium (II)) (vpy is 4-vinylpyridine). A bilayer film assembly consisting of poly-[(bpy)2 Ru(vpy) 2]2+ as an inner film and the aforementioned copolymer of Ru/Re yields even greater reactivity to CO2; a method of forming a polymeric film on an electrode; and a method of reducing CO2 to CO using an electrode having a polymeric film adsorbed to its surface.

Yacynych, U.S. Pat. No. 5,540,828 for a Method for making electrochemical sensors and biosensors having a polymer modified surface discloses a method for making a sensing element for use in a sensor or biosensor that amperometrically measures the concentration of an analyte in a liquid, includes the following sequential steps: a) obtaining an electrode; b) immersing the electrode in a solution of monomer that is capable of being electropolymerized into an electrically insulating polymer; c) flowing an electric current from a cathode through the solution to the electrode at a voltage and amperage sufficient to cause the monomer to polymerize on the surface of the electrode, thereby yielding an electrode coated with an adherent layer of electrically insulating polymer; and e) impregnating the polymeric coating on the surface with a sensing agent that is capable, when contacted by a specific analyte in a chemical or biological liquid, of generating an electroactive molecule that can be detected amperometrically.

Yacynych et al, U.S. Pat. No. 5,286,364 for a Surface-modified electochemical biosensor discloses a biosensor.

Wilson et al., U.S. Pat. No. 6,814,845 for a Method for depositing an enzyme on an electrically conductive substrate discloses improved biosensors are provided having excellent selectivity and stability properties, together with methods of preparing the biosensors. A preferred biosensor includes an electrode having enzyme deposited thereon together with a layer of electropolymerized polymer intermingled with the enzyme; a crosslinked silane film is applied over the polymer layer, and a final coating of polyurethane is formed over the film. In preparative procedures, the enzyme is electrodeposited using an aqueous enzyme solution containing a nonionic surfactant at a concentration level preferably in excess of the critical micelle concentration of the surfactant. In the case of a glucose sensor, the polymer layer is preferably polyphenol, while the silane film is crosslinked (3-aminopropyl) trimethoxysilane. The preferred biosensors have greatly enhanced selectivity stabilities.

Haesik et al., U.S. Pat. No. 6,413,396 for an Enzyme electrode sensor and manufacturing method thereof discloses an enzyme electrode sensor and a fabricating method thereof, and more particularly, an enzyme electrode sensor which is a biosensor using electrochemical measurement and a manufacturing method thereof. The sensor includes an electrode, a first nonconducting polymer layer formed by electropolymerization outside the electrode wherein enzyme is immobilized in the nonconducting polymer layer, a second nonconducting polymer layer in which enzyme is not immobilized, the second nonconducting layer formed by electropolymerization outside the first nonconducting polymer layer, and an outer layer formed outside the second nonconducting layer. The sensor selectivity is improved as the interference of organic materials is inhibited, and the interference of acetaminophen causing the major problem with a glucose sensor is controlled effectively by the sensor.

Tissue-penetrating electrochemical sensors represent a promising avenue towards the minimally-invasive quantification of a number of relevant analytes in the physiological fluid, such as interstitial fluid, blood, serum, and plasma. Currently, to impart the ability to selectively quantify chemical/biochemical analytes of interest, membranes comprising of one or more polymers with a biorecognition element dispersed therein are cast in a manual fashion, keeping costs high and sensor-to-sensor uniformity low. In this application, tissue can refer to, but is not limited to, skin, organs, and cells.

Prior art solutions have been concerned with the immobilization of biorecognition elements by means of entrapment in a polymeric membrane cast by a manual, human-operated process (via dip or drop casting in an aqueous- or solvent-based solution of polymer and enzyme) or by means of the assistance of an automated liquid reagent dispensing robot. This is a serialized process and, as a consequence, low throughput and high device cost are challenges that still confront skin- and tissue-penetrating electrochemical sensor production. When performed by a human operator, such deposition processes often result in a sensor response characterized by a wide degree of variance and hence sensors for clinical applications must often undergo quality control or calibration measures on an individual basis, thereby further impeding the transition to mass production techniques.

BRIEF SUMMARY OF THE INVENTION

The technology disclosed herein addresses the above challenges by disclosing a method for the automated and parallelized co-deposition of a conducting polymer and biorecognition element at one or more working electrodes of a tissue-penetrating electrochemical sensor.

The present invention provides for a method to impart the ability to selectively quantify chemical/biochemical analytes occupying physiological fluids via an automated process that allow the precise and spatially-defined simultaneous deposition of a thin-film of polymer containing an immobilized biorecognition element dispersed therein.

The technology described herein also involves a method for automated, volume-scale functionalization of a tissue-penetrating electrochemical sensor to yield selective chemical or biochemical recognition capability in vivo.

The present invention delineates a method for the simultaneous co-deposition of both an entrapment polymer and an immobilized biorecognition element onto at least one working electrode using an electro-deposition process for skin- and tissue-penetrating electrochemical sensor functionalization that is highly amenable to high-throughput, automated, parallelized, and highly reproducible manufacturing methods that do away with the need for a human operator during the sensor functionalization process. Indeed, with the trend towards increasing sensor miniaturization, conventional manual processes associated with sensor functionalization to impart a selective biorecognition capability is becoming increasingly inaccessible using a human operator and the need remains for a sensor functionalization strategy that can be exploited along conventional precision manufacturing lines, such as those used for the medical device, MEMS, and semiconductor industries.

One aspect of the present invention is a tissue-penetrating electrochemical sensor device for the quantification of a chemical or biochemical entity in a physiological fluid. The device comprises a tissue-penetrating electrochemical sensor comprising at least one spatially-defined working electrode, and a conducting polymer film comprising an organic electroactive monomer precursor and at least one biorecognition element. The organic electroactive monomer precursor and the at least one biorecognition element dispersed uniformly and physically entrapped in the conducting polymer film. The conducting polymer film is produced by immersing the tissue-penetrating electrochemical sensor in a solution containing the at least one biomolecular recognition element and the organic electroactive monomer precursor which is dissolved in the solution, and wherein application of an oxidizing potential or a reducing potential at the spatially-defined working electrode causes the co-electrodeposition of the conducting polymer film.

Another aspect of the present invention is a method for the fabrication of a tissue-penetrating electrochemical sensor for the quantification of a chemical or biochemical entity in a physiological fluid. The method includes immersing a tissue-penetrating electrochemical sensor comprising at least one spatially-defined working electrode in a solution comprising at least one biomolecular recognition element and an organic electroactive monomer precursor dissolved in the solution. The method also includes applying of an oxidizing potential or a reducing potential at the spatially-defined working electrode, causing a co-electrodeposition of a polymer film from the organic electroactive monomer precursor and the at least one biorecognition element dispersed uniformly and physically entrapped in the polymer film.

The organic electroactive monomer precursor is preferably selected for at least one of its perm-selective properties following conversion to a thin-film of polymer, its charge rejection properties following conversion to a thin-film of polymer, its anti-biofouling properties following conversion to a thin-film of polymer, its porosity following conversion to a thin-film of polymer, its diffusion-limiting nature following conversion to a thin-film of polymer, or its self-limited growth during conversion to a thin-film of polymer.

The biomolecular recognition element comprises at least one of an enzyme, biocatalyst, inorganic catalyst, ion-selective material, antibody, oligonucleotide, electrochemical redox mediator, cell, or organelle.

The tissue-penetrating electrochemical sensor further comprises at least a reference electrode or a counter electrode.

The oxidizing potential or reducing potential is either a fixed potential or a time-varying potential.

The oxidizing potential or reducing potential is applied using one of an amperometric technique, a voltammetric technique, a conductometric technique, or a coulometric technique.

The oxidizing potential or the reducing potential is selected to result in the formation of a precise thickness of the conducting polymer film.

The oxidizing potential or the reducing potential is applied for a specified time duration to result in the formation of a precise thickness of the conducting polymer film.

The oxidizing potential or the reducing potential is selected to pass a specified amount of charge through at least one of the working electrode to result in the formation of a precise thickness of the conducting polymer film.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

One embodiment is a tissue-penetrating electrochemical sensor device for the quantification of a chemical or biochemical entity in a physiological fluid. The device preferably comprises a tissue-penetrating electrochemical sensor comprising at least one spatially-defined working electrode, and a conducting polymer film comprising an organic electroactive monomer precursor and at least one biorecognition element. The organic electroactive monomer precursor and the at least one biorecognition element dispersed uniformly and physically entrapped in the conducting polymer film. The conducting polymer film is produced by immersing the tissue-penetrating electrochemical sensor in a solution containing the at least one biomolecular recognition element and the organic electroactive monomer precursor which is dissolved in the solution, and wherein application of an oxidizing potential or a reducing potential at the spatially-defined working electrode causes the co-electrodeposition of the conducting polymer film.

Another embodiment is a method for the fabrication of a tissue-penetrating electrochemical sensor for the quantification of a chemical or biochemical entity in a physiological fluid. The method includes immersing a tissue-penetrating electrochemical sensor comprising at least one spatially-defined working electrode in a solution comprising at least one biomolecular recognition element and an organic electroactive monomer precursor dissolved in the solution. The method also includes applying of an oxidizing potential or a reducing potential at the spatially-defined working electrode, causing a co-electrodeposition of a polymer film from the organic electroactive monomer precursor and the at least one biorecognition element dispersed uniformly and physically entrapped in the polymer film.

The method provides for reliably dispensing a reagent containing at least one biorecognition at the micron-scale, as required to functionalize microelectrodes and microelectrode arrays. The method provides the formation of a polymeric film containing a biorecognition element by means of electro-polymerization enables the precise control of the thickness of the layer as well as the formation of a very thin layer. Past conventional methods of forming a polymeric layer by use of drop casting, dip coating, spin coating, or dispensing had the difficulty of controlling the thickness of the layer, thereby forming a relatively thick and non-uniform layer. Therefore, electro-polymerization utilized in the present invention is very effective for the reproducible formation of a layer as well as the simultaneous realization of co-deposition of both the polymer and the biorecognition element.

In addition to variations in film thickness caused by conventional sensor functionalization approaches, these techniques require multiple steps to create a selective, diffusion-limiting, interference-rejecting sensor membrane and it is the case that a polymeric film is cast on the electrode following a prior biorecognition element deposition step, which further contributes to decreased sensor uniformity and increased manufacturing cost and time. The simultaneous co-deposition of both the polymer and the biorecognition element, as disclosed in the current invention, serve to mitigate these challenges that have plagued the electrochemical sensor industry for some time.

Precisely-defined thin-films, whose thickness and porosity can be precisely controlled by the suitable application of voltage, current, or charge that is passed through the electrode, also embody the advantage that the approach requires minimal quantity of reagent, thereby contributing to a reduction in cost to manufacture.

The technology disclosed herein discloses a method for the automated and parallelized co-deposition of a conducting polymer and biorecognition element at one or more working electrodes of a tissue-penetrating electrochemical sensor. The method involves the immersion of the electrochemical sensor in a solution of an organic electroactive monomeric precursor (to the conducting polymer) and biorecognition element (enzyme, antibody, etc.) and applying a fixed- or time-varying potential at one or more of the working electrodes to instigate co-electrodeposition. This encourages the electro-polymerization of a conducting polymer film, synthesized from the monomeric precursor, onto the working electrode surface. Because it is uniformly dispersed in solution and often is a large molecule (larger than the pore size of the polymer), the biorecognition element is also entrapped, in a spatially uniform fashion, in the polymer film and can, optionally, serve as the counter-ion or dopant during the electro-polymerization process through suitable choice of a biorecognition element with appropriate isoelectric point and solution pH.

Leveraging this self-assembly process, which is also self-limiting, the thickness and porosity of the polymeric film is adjusted via modification of the applied potential, current, or charge passed through the electrochemical cell during the co-electrodeposition process. This has wide-ranging implications pertaining to the sensitivity, selectivity, stability, and response time of the as-synthesized tissue-penetrating electrochemical sensor.

The disclosed technique facilitates spatially-defined deposition of precisely-controlled thin-films on one or more working electrode surfaces and allows the sensor designer to synthesize entrapment membranes to achieve certain utilitarian features such as co-circulating electroactive interference rejection (via perm- or charge-selectivity), increased linearity, extended lifetime, minimal signal drift, or reduced tendency to undergo biofouling when used in vivo.

Simple and reproducible formations of chemically- and biochemically-selective polymer films can be formed with the disclosed method, which obviates the need for multiple biorecognition element casting and polymer casting steps by allowing for the simultaneous co-deposition of a thin-film containing both an entrapping polymer and biorecognition element. As such, the as-disclosed sensor functionalization strategy enables parallelized sensor functionalization without human intervention and is amenable to implementation along assembly lines or semiconductor fabrication processes.

The following commercially-available components are used in the synthesis of the sensor:

The voltage/current source is preferably a CH INSTRUMENTS Model 10000 Series Multi-Potentiostat, Metrohm Autolab PGSTAT Series Potentiostat Galvanostat, or Palmsens EmStat Potentiostat. The voltages utilized depend on the film, and generally range from −0.2 volts to +1.0 volts. The current transduced ranges from 10 picoAmperes (pA) to 100 microAmperes (µA), and is dependent on whether a singular electrode is electro-deposited or if multiple electrodes are electro-deposited as a group.

The working electrode is preferably a CH INSTRUMENTS CH101 2 mm-diameter gold disc microelectrode, or a METROHM MF-2150 100 µm-diameter platinum disc microelectrode.

The tissue-penetrating electrochemical sensor is preferably a subcutaneous, percutaneous, transdermal, or intradermal sensor in which an electrical stimulus is applied to encourage a redox reaction and in which a voltage, current, charge, resistance, or impedance property is measured to infer the concentration of a particular chemical/biochemical analyte of interest present in the physiological fluid compartment in which the sensor is located. The sensor also comprises at least one working electrode (defined below) and at least one of a counter electrode and a reference electrode.

The working electrode is preferably a spatially-defined electrode whereby the electrochemical sensing operation is to occur; functionalized with a polymer and biorecognition element to impart the selective ability to transduce the chemical/biochemical of interest into an electrical signal. A defined voltage, current, or amount of charge is applied as a stimulus to the working electrode to instigate a redox reaction and a voltage, current, charge, resistance, or impedance response is measured to infer the concentration of a particular chemical/biochemical analyte of interest.

The organic electroactive monomer precursor is preferably an organic monomer that is either oxidized or reduced by the application of a suitable voltage, current, or amount of charge on a working electrode surface and concomitantly electro-deposited/electro-polymerized on the working electrode surface from a solution in which it is dissolved.

The biorecognition element is preferably an organic, inorganic, or biological compound that selectively binds, catalyzes, or sieves a particular chemical/biochemical analyte of interest and, in doing so, changes its electrical properties (voltage, current, charge, resistance, or impedance) or produces an electroactive product ($H_2O_2$, NADH, etc.). Examples of a biorecognition element include, but are not limited to, an enzyme, biocatalyst, inorganic catalyst, ion-selective material, antibody, oligonucleotide, electrochemical redox mediator, cell, or organelle.

The conducting polymer is preferably synthesized from the organic electroactive monomer precursor through the process of electro-polymerization. The conducting polymer serves to physically entrap the biorecognition element in its highly porous matrix, thereby forming a thin-film with selective sensing capabilities. Alternatively, the biorecognition element can serve as the dopant or counter-ion through the appropriate selection of the biorecognition element's isoelectric point and solution pH in which the organic electroactive monomer precursor and biorecognition element are dissolved. The polymer can also be selected to exhibit perm-selective, charge-selective, size-selective, or anti-biofouling properties. The polymer film thickness preferably ranges from 5 nanometers ("nm") to 50 nm. The thickness is primarily governed by the voltage applied, the time that the voltage is applied, the amount of the monomeric precursor in the solution, and the geometry of the electrode. The porosity of the film and the perm-selectivity of the film are also adjusted by these factors.

The voltage or current source is either a power supply, potentiostat, galvanostat, function generator, or any source of electrical voltage or current. The voltage or current source is operated to apply a particular voltage, current, or amount of charge. The voltage or current source is terminated once a certain amount of time has transpired or charge has passed through the working electrode. The voltages utilized depend on the film and generally range from −0.2 volts to +1.0 volts. The current transduced ranges from 10 picoAmperes (pA) to 100 microAmperes (µA), and is dependent on whether a singular electrode is electro-deposited or if multiple electrodes are electro-deposited as a group.

The solution composition comprises the organic electroactive monomeric precursor dissolved in $H_2O$ and optionally salt(s) from the group consisting of NaCl, KCl, MgSO4, CaCl2, Na2HPO4, NaH2PO4, K2HPO4, and KH2PO4. The organic monomeric precursor is preferably one or more of, but not limited to, the following: aniline, pyrrole, acetylene, phenylene, phenylene vinylene, phenylene diamine, thiophene, 3,4-ethylenedioxythiophene, aminophenylboronic acid.

The method steps of the invention include the following:
1) Immersion of a tissue-penetrating electrochemical sensor in a solution of at least one of a biorecognition element and an organic electroactive monomer precursor. A tissue-penetrating electrochemical sensor 100 containing, in this example, exactly one counter electrode 101, one working electrode 102, and one reference electrode 103 is immersed in a solution 104 comprising at least one of a biomolecular recognition element and at least one of an organic electroactive monomer precursor dissolved in said solution. In a two-electrode embodiment, a tissue-penetrating electrochemical sensor 100 containing, in this example, exactly one working electrode 102 and one reference electrode 103 is immersed in a solution 104 comprising at least one of a biomolecular recognition element and at least one of an organic electroactive monomer precursor dissolved in said solution. 2) Application of an oxidizing or reducing potential upon at least one working electrode contained in electrochemical sensor. A voltage or current source 105 is connected, in an ohmic fashion, to counter electrode 101 and at least one of 102 and 103; a constant or time-varying potential is applied to counter electrode 101 to pass a controlled and pre-determined amount of current or charge through counter electrode 101. 3) Simultaneous co-electrodeposition of a thin-film of polymer comprised of organic electroactive monomer precursor and the at least one biorecognition element. Following the application of a potential, current, or charge, the formation of a thin-film, typically on the order of 1-100 nm, of the polymerized organic electroactive monomer, serves to entrap the biomolecular recognition element in the highly porous matrix created therein. This processes functionalizes the working electrode 102 of the tissue-penetrating electrochemical sensor and allows it to achieve the selective quantification of at least one chemical or biochemical analyte in a physiological fluid.

The inputs of the invention are as follow:
1) an organic electroactive monomer precursor. The organic monomer is either oxidized or reduced by the application of a suitable voltage, current, or amount of charge on a working electrode surface and concomitantly electro-deposited/electro-polymerized on the working electrode surface from a solution in which it is dissolved.

2) Biorecognition element. An organic, inorganic, or biological compound that selectively binds, catalyzes, or sieves a particular chemical/biochemical analyte of interest and, in doing so, changes its electrical properties (voltage, current, charge, resistance, or impedance) or produces an electroactive product ($H_2O_2$, NADH, etc.). Examples of a biorecognition element include, but are not limited to, an enzyme, biocatalyst, inorganic catalyst, ion-selective material, antibody, oligonucleotide, electrochemical redox mediator, cell, or organelle.

3) Electrical stimulus. A specified and controlled voltage, current, or amount of charge is applied. The electrical stimulus is terminated once a certain amount of time has transpired or charge has passed through the system.

Figure 9:
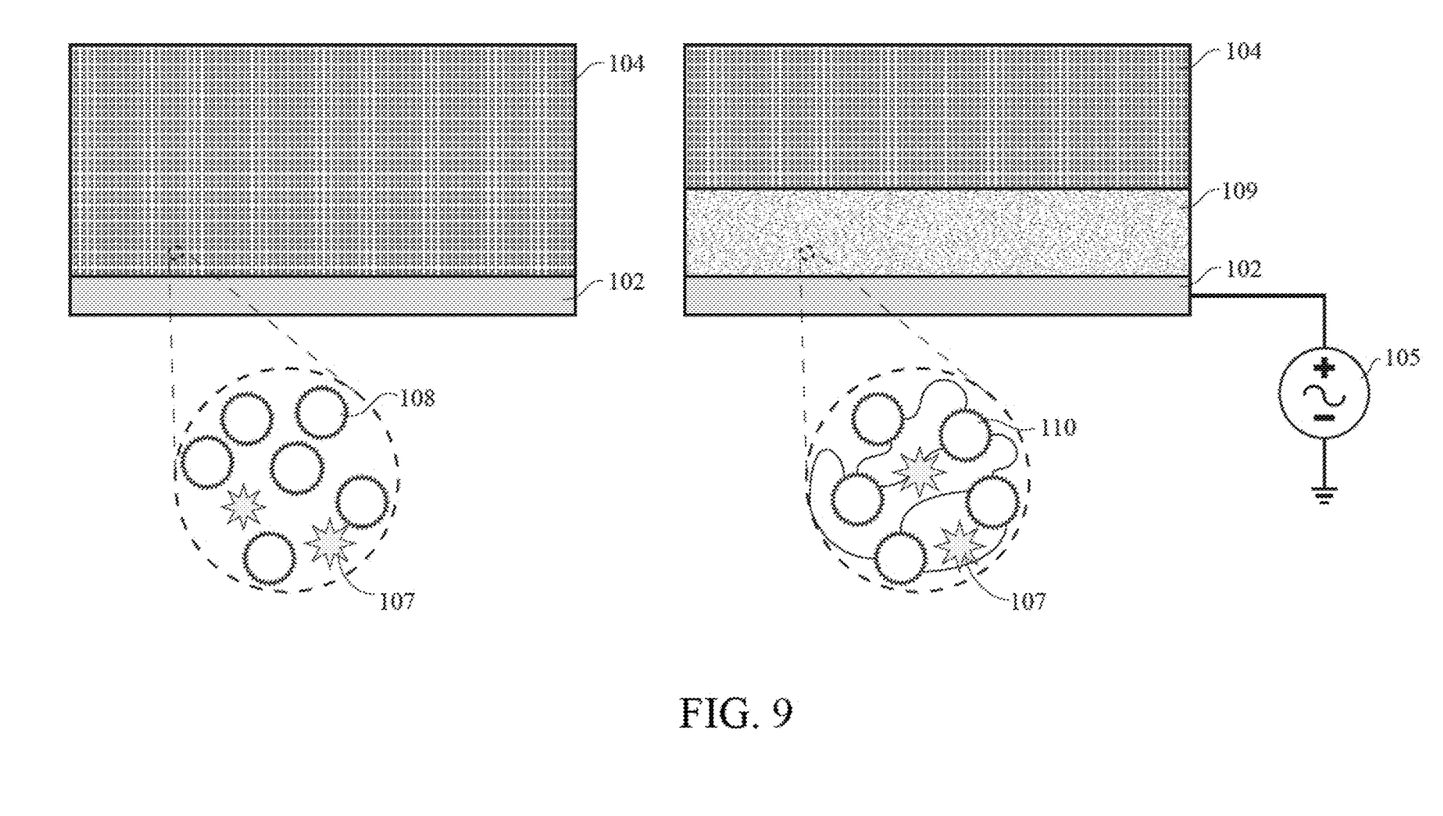
FIG. 9 is a schematic representation delineating the co-electrodeposition of a polymer-biorecognition element film on at least one working electrode of a tissue-penetrating electrochemical sensor.

The outputs of the invention are as follows: Functionalized working electrode. One or more working electrodes are coated with a thin-film, typically on the order of 1-100 nm, of the polymerized organic electroactive monomer 110, which serves to entrap the biomolecular recognition element to form a co-deposited, highly porous polymer-biorecognition element matrix 109. This processes functionalizes the working electrode 102 of the tissue-penetrating electrochemical sensor and allows it to achieve the selective quantification of at least one chemical or biochemical analyte in a physiological fluid.

Figure 1:
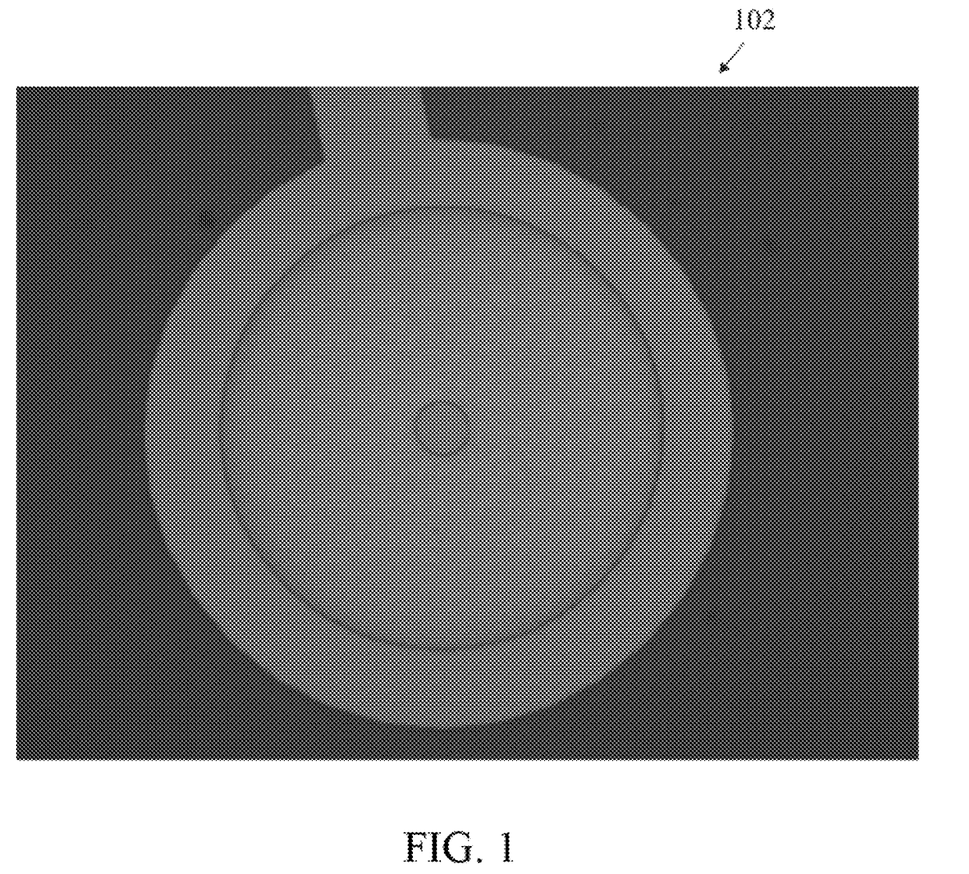
FIG. 1 is an optical micrograph of an unfunctionalized working electrode.

FIG. 1 is an optical micrograph of an unfunctionalized working electrode.

Figure 2:
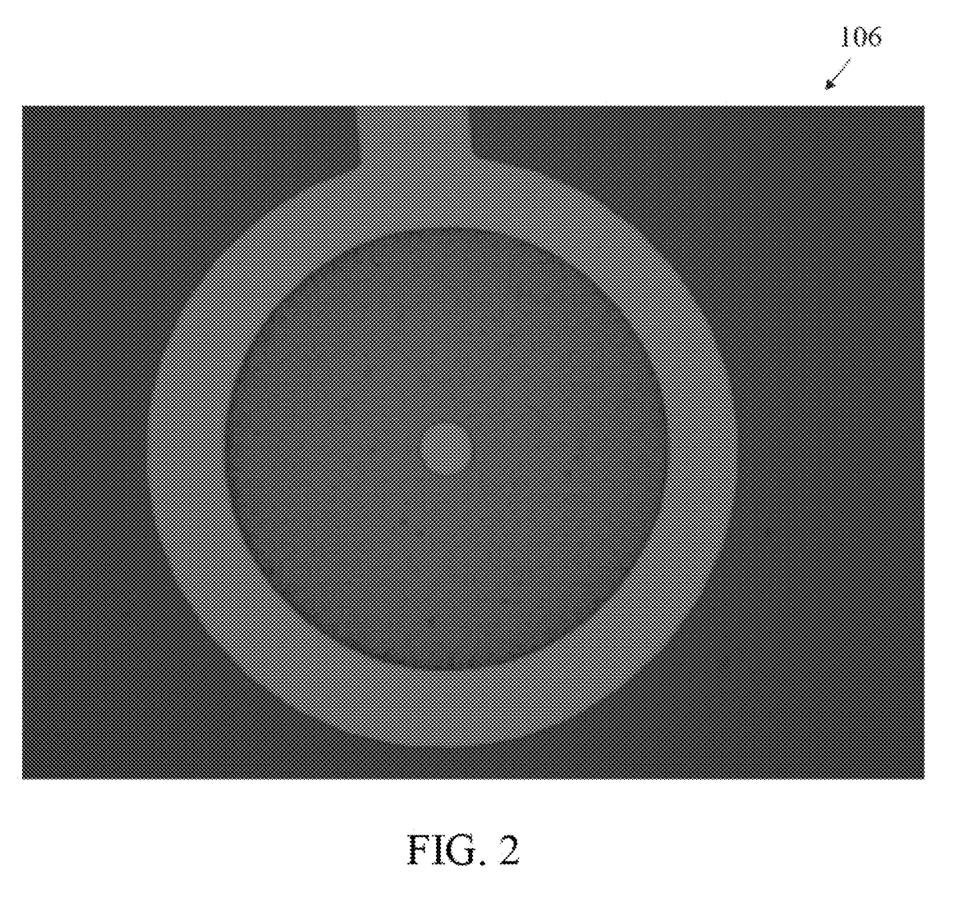
FIG. 2 is an optical micrograph of the working electrode shown in FIG. 1 following functionalization.

FIG. 2 is an optical micrograph of the working electrode shown in FIG. 1 following functionalization. The presence of a thin-film of co-electrodeposited polymer and enzyme can be observed from the image.

Figure 3:
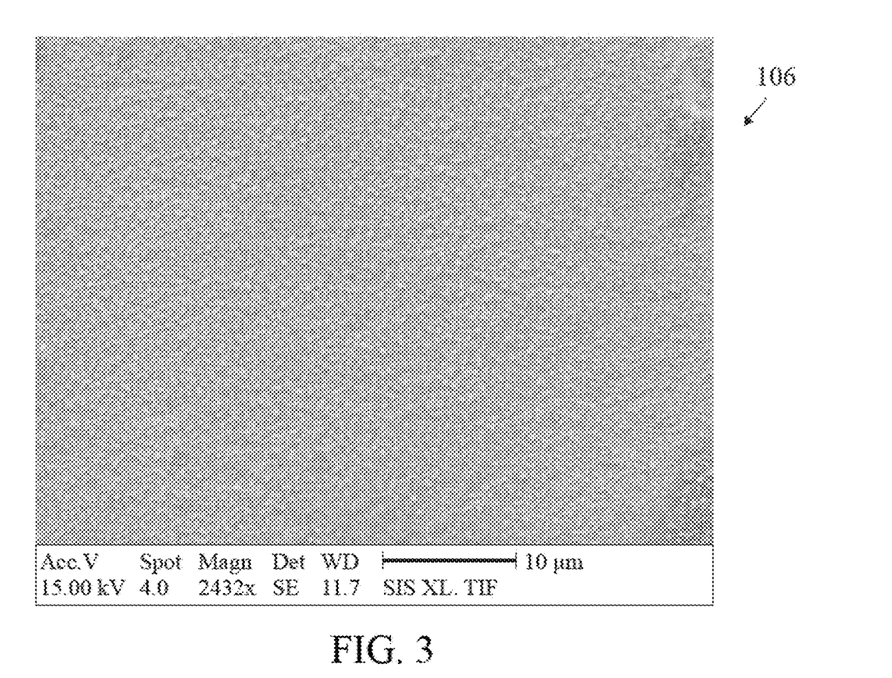
FIG. 3 is an electron micrograph delineating the surface morphology of the functionalized working electrode provided in FIG. 2.

FIG. 3 is an electron micrograph delineating the surface morphology of the functionalized working electrode provided in FIG. 2.

Figure 4:
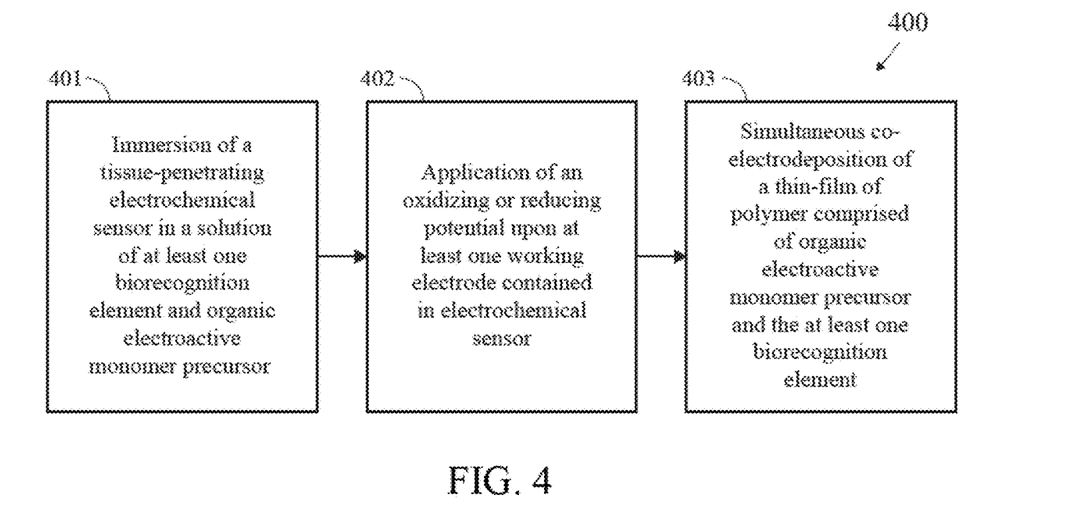
FIG. 4 is a block/process flow diagram illustrating the major constituents involved in the functionalization of a tissue- or skin-penetrating electrochemical sensor to facilitate chemical or biochemical quantification of various analytes in physiological fluids.

FIG. 4 is a block/process flow diagram illustrating the major constituents involved in the functionalization of a tissue- or skin-penetrating electrochemical sensor to facilitate chemical or biochemical quantification of various analytes in physiological fluids.

Figure 5:
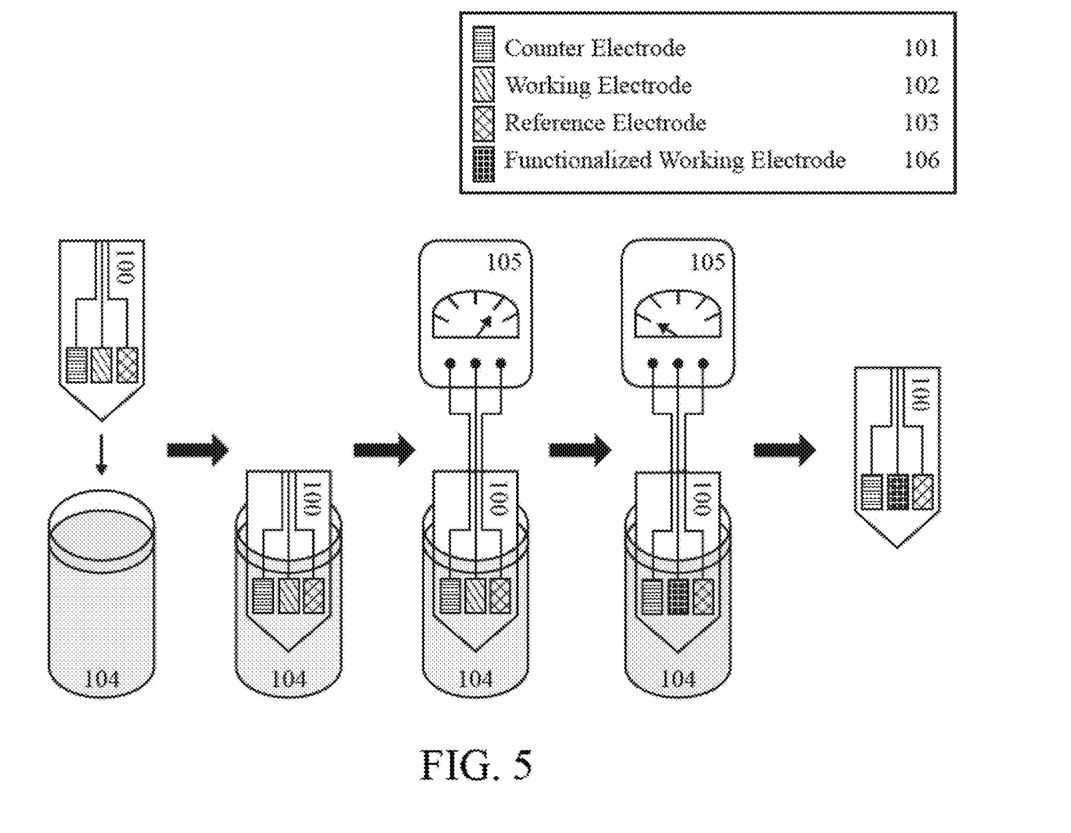
FIG. 5 is a schematic illustration delineating the major steps involved in the co-electrodeposition of a polymer-biorecognition element film on at least one working electrode of a tissue-penetrating three-electrode electrochemical sensor.

FIG. 5 is a schematic illustration delineating the major steps involved in the co-electrodeposition of a polymer-biorecognition element film on at least one working electrode of a tissue-penetrating three-electrode electrochemical sensor. Briefly, a tissue-penetrating electrochemical sensor 100 containing, in this example, exactly one counter electrode 101, one working electrode 102, and one reference electrode 103 is immersed in a solution 104 comprising at least one of a biomolecular recognition element and at least one of an organic electroactive monomer precursor dissolved in said solution. A voltage or current source 105 is connected, in an ohmic fashion, to 102 and at least one of 101 and 103; a constant or time-varying potential is applied to 102 to pass a controlled and pre-determined amount of current or charge through 102. This, in turn, instigates the formation of a thin-film, typically on the order of 1-100 nm, of the polymerized organic electroactive monomer, which serves to entrap the said biomolecular recognition element in the highly porous matrix created therein. This processes functionalizes the working electrode of the tissue-penetrating electrochemical sensor and allows it to achieve the selective quantification of at least one chemical or biochemical analyte in a physiological fluid.

Figure 6:
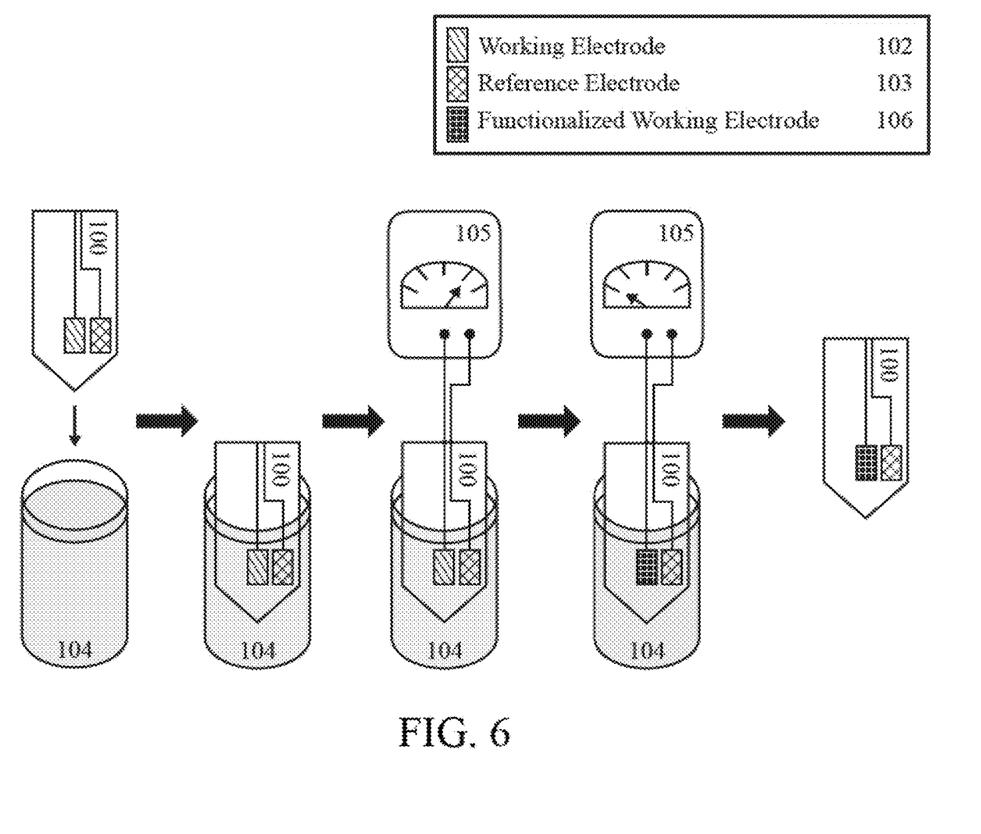
FIG. 6 is a schematic illustration delineating the major steps involved in the co-electrodeposition of a polymer-biorecognition element film on at least one working electrode of a tissue-penetrating two-electrode electrochemical sensor.

FIG. 6 is a schematic illustration delineating the major steps involved in the co-electrodeposition of a polymer-biorecognition element film on at least one working electrode of a tissue-penetrating two-electrode electrochemical sensor. Briefly, a tissue-penetrating electrochemical sensor 100 containing, in this example, exactly one working electrode 102 and one reference electrode 103 is immersed in a solution 104 comprising at least one of a biomolecular recognition element and at least one of an organic electroactive monomer precursor dissolved in said solution. A voltage or current source 105 is connected, in an ohmic fashion, to 102 and 103; a constant or time-varying potential is applied to 102 to pass a controlled and pre-determined amount of current or charge through 102. This, in turn, instigates the formation of a thin-film, typically on the order of 1-100 nm, of the polymerized organic electroactive monomer, which serves to entrap the said biomolecular recognition element in the highly porous matrix created therein. This processes functionalizes the working electrode of the tissue-penetrating electrochemical sensor and allows it to achieve the selective quantification of at least one chemical or biochemical analyte in a physiological fluid.

Figure 7:
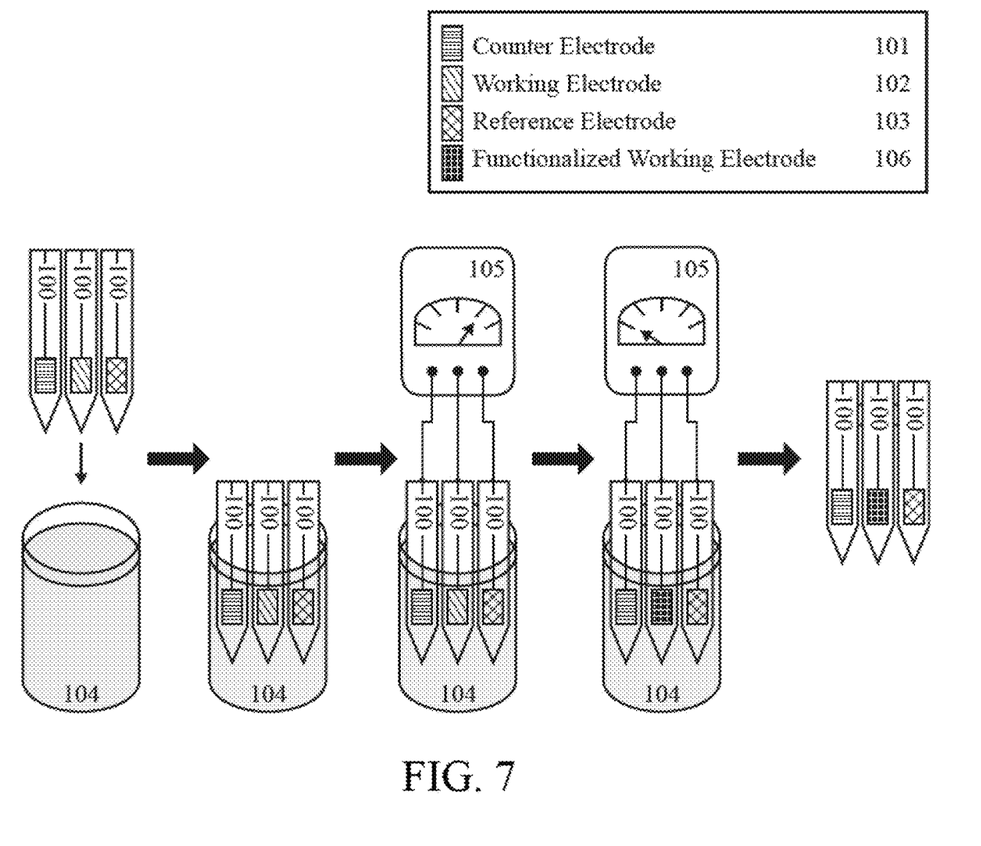
FIG. 7 is a schematic illustration delineating the major steps involved in the co-electrodeposition of a polymer-biorecognition element film on at least one working electrode of a multi-component tissue-penetrating three-electrode electrochemical sensor, whereby each electrode is located within an isolated tissue-penetration electrochemical sensor.

FIG. 7 is a schematic illustration delineating the major steps involved in the co-electrodeposition of a polymer-biorecognition element film on at least one working electrode of a multi-component tissue-penetrating three-electrode electrochemical sensor, whereby each electrode is located within an isolated tissue-penetration electrochemical sensor. Briefly, three tissue-penetrating electrochemical sensors 100 containing, in this example, exactly one counter electrode 101, one working electrode 102, and one reference electrode 103 are immersed in a solution 104 comprising at least one of a biomolecular recognition element and at least one of an organic electroactive monomer precursor dissolved in said solution. A voltage or current source 105 is connected, in an ohmic fashion, to 102 and at least one of 101 and 103; a constant or time-varying potential is applied to 102 to pass a controlled and pre-determined amount of current or charge through 102. This, in turn, instigates the formation of a thin-film, typically on the order of 1-100 nm, of the polymerized organic electroactive monomer, which serves to entrap the said biomolecular recognition element in the highly porous matrix created therein. This processes functionalizes the working electrode of the tissue-penetrating electrochemical sensor and allows it to achieve the selective quantification of at least one chemical or biochemical analyte in a physiological fluid.

Figure 8:
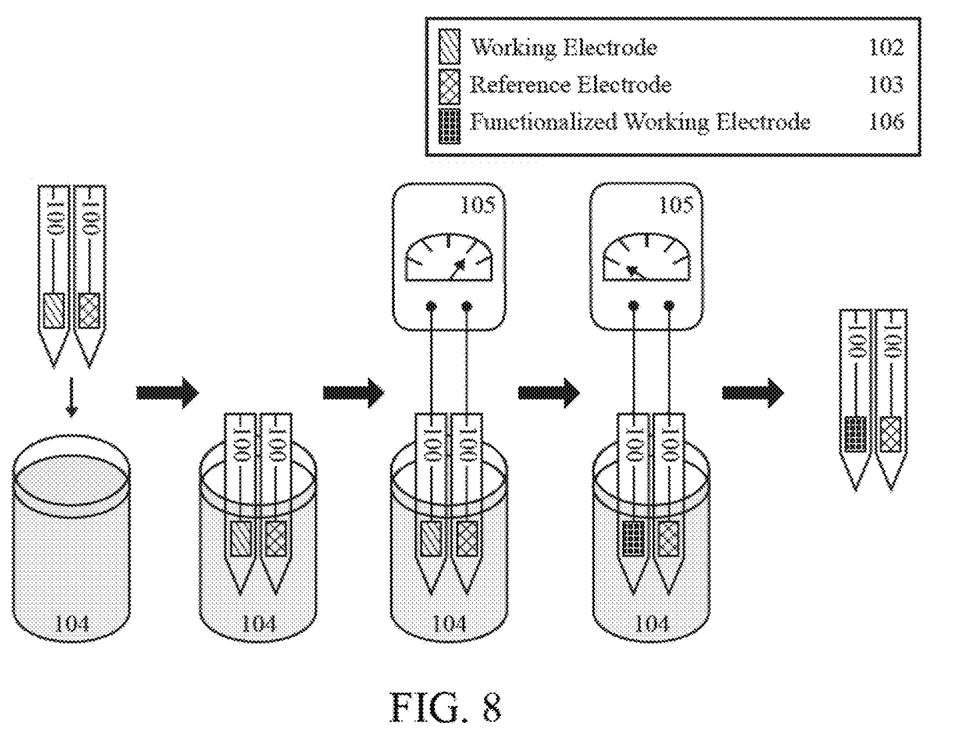
FIG. 8 is a schematic illustration delineating the major steps involved in the co-electrodeposition of a polymer-biorecognition element film on at least one working electrode of a tissue-penetrating two-electrode electrochemical sensor.

FIG. 8 is a schematic illustration delineating the major steps involved in the co-electrodeposition of a polymer-biorecognition element film on at least one working electrode of a tissue-penetrating two-electrode electrochemical sensor. Briefly, two tissue-penetrating electrochemical sensors 100 containing, in this example, exactly one working electrode 102 and one reference electrode 103 are immersed in a solution 104 comprising at least one of a biomolecular recognition element and at least one of an organic electroactive monomer precursor dissolved in said solution. A voltage or current source 105 is connected, in an ohmic fashion, to working electrode 102 and reference electrode 103; a constant or time-varying potential is applied to working electrode 102 to pass a controlled and pre-determined amount of current or charge through working electrode 102. This, in turn, instigates the formation of a thin-film, typically on the order of 1-100 nm, of the polymerized organic electroactive monomer, which serves to entrap the said biomolecular recognition element in the highly porous matrix created therein. This processes functionalizes the working electrode of the tissue-penetrating electrochemical sensor and allows it to achieve the selective quantification of at least one chemical or biochemical analyte in a physiological fluid.

FIG. 9 is a schematic representation delineating the co-electrodeposition of a polymer-biorecognition element film on at least one working electrode 102 of a tissue-penetrating electrochemical sensor. The working electrode 102 in this example is immersed in a solution 104 comprising at least one of a biomolecular recognition element (107 in inset) and at least one of an organic electroactive monomer precursor (108 in inset) dissolved in said solution. A voltage or current source 105 is connected, in an ohmic fashion, to working electrode 102; a constant or time-varying potential is applied to working electrode 102 to pass a controlled and pre-determined amount of current or charge through working electrode 102. This, in turn, instigates the formation of a thin-film, typically on the order of 1-100 nm, of the polymerized organic electroactive monomer (110 in inset), which serves to entrap the biomolecular recognition element to form a co-deposited, highly porous polymer-biorecognition element matrix 109. This processes functionalizes the working electrode 102 of the tissue-penetrating electrochemical sensor 100 and allows it to achieve the selective quantification of at least one chemical or biochemical analyte in a physiological fluid.

McCanna et al., U.S. patent application Ser. No. 14/843,926, filed on Sep. 2, 2015, for a Miniaturized Sub-Nanoampere Sensitivity Low-Noise Potentiostat System is hereby incorporated by reference in its entirety.

Windmiller, U.S. Provisional Patent Application No. 62/233,323, filed on Sep. 26, 2015, for a Methods And Devices For Embedding Sensors In Container Labels and Packaging is hereby incorporated by reference in its entirety.

Windmiller et al., U.S. Provisional Patent Application No. 62/233,324, filed on Sep. 26, 2015, for a Method And System For Manufacturing Microneedles With Electrodes is hereby incorporated by reference in its entirety.

Windmiller et al., U.S. Provisional Patent Application No. 62/247,732, filed on Oct. 28, 2015, for a Method And System For Three Dimensional Printing Of Microneedles And Microneedle Arrays For Transdermal Biosensing And Drug Delivery is hereby incorporated by reference in its entirety.

Windmiller et al., U.S. Provisional Patent Application No. 62/247,730, filed on Oct. 28, 2015, for a Sensors For Wearable Devices is hereby incorporated by reference in its entirety.

Windmiller et al., U.S. patent application Ser. No. 14/955,850, filed on Dec. 1, 2015, for a Method And Apparatus For Determining Body Fluid Loss is hereby incorporated by reference in its entirety.

Windmiller, U.S. Provisional Patent Application No. 62/307,444, filed on Mar. 12, 2016, for a Method And Apparatus For Determining Exhaled Carbon Loss is hereby incorporated by reference in its entirety.

Windmiller, U.S. Provisional Patent Application No. 62/307,445, filed on Mar. 12, 2016, for a Method And System For Determining Physiological and Environmental Strain Indices is hereby incorporated by reference in its entirety.

Windmiller, U.S. patent application Ser. No. 15/177,289, filed on Jun. 8, 2016, for a Methods And Apparatus For Interfacing A Microneedle-Based Electrochemical Biosensor With An External Wireless Readout Device is hereby incorporated by reference in its entirety.

Wang et al., U.S. Patent Publication Number 20140336487 for a Microneedle Arrays For Biosensing And Drug Delivery is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

I claim as my invention the following:

1. A tissue-penetrating electrochemical sensor device for the quantification of a chemical or biochemical entity in a physiological fluid, the device comprising:

a tissue-penetrating electrochemical sensor comprising a working electrode, a counter electrode and a reference electrode;

a conducting polymer film comprising an organic electroactive monomer precursor and at least one biomolecular recognition element, the at least one biomolecular recognition element entrapped in a spatially uniform manner in the conducting polymer film, wherein the biomolecular recognition element comprises at least one of a biocatalyst, an inorganic catalyst, an ion-selective material, an antibody, an oligonucleotide, an electrochemical redox mediator, a cell, or an organelle, wherein the organic electroactive monomer precursor is selected for at least one of its charge rejection properties following conversion to a thin-film of polymer, its anti-biofouling properties following conversion to a thin-film of polymer, its porosity following conversion to a thin-film of polymer, its diffusion-limiting nature following conversion to a thin-film of polymer, or its self-limited growth during conversion to a thin-film of polymer, wherein the organic electroactive monomer precursor is at least one of aniline, pyrrole, acetylene, phenylene, phenylene vinylene, phenylene diamine, thiophene, 3,4-ethylenedioxythiophene, or aminophenylboronic acid;

wherein the conducting polymer film is produced by immersing the tissue-penetrating electrochemical sensor in a solution containing the at least one biomolecular recognition element and the organic electroactive monomer precursor which is dissolved in the solution, and wherein application of an oxidizing potential or a reducing potential at the working electrode causes the co-electrodeposition of the conducting polymer film.

2. The device of claim 1 wherein the oxidizing potential or reducing potential is either a fixed potential or a time-varying potential.

3. The device of claim 2 wherein the oxidizing potential or reducing potential is applied using one of an amperometric technique, a voltammetric technique, a conductometric technique, or a coulometric technique.

4. The device of claim 2 wherein the oxidizing potential or the reducing potential is selected to result in the formation of a thickness of the conducting polymer film ranging from 5 to 50 nanometers.

5. The device of claim 2 wherein the oxidizing potential or the reducing potential is applied for a specified time duration to result in the formation of a thickness of the conducting polymer film ranging from 5 to 50 nanometers.

6. The device of claim 2 wherein the oxidizing potential or the reducing potential is selected to pass a specified amount of charge through at least one of the working electrode to result in the formation of a thickness of the conducting polymer film ranging from 5 to 50 nanometers.

7. A method for the fabrication of a tissue-penetrating electrochemical sensor for the quantification of a chemical or biochemical entity in a physiological fluid, the method comprising:
immersing a tissue-penetrating electrochemical sensor comprising at least one working electrode in a solution comprising a biomolecular recognition element and an organic electroactive monomer precursor dissolved in the solution;
applying of an oxidizing potential or a reducing potential at the working electrode, causing a co-electrodeposition on the working electrode of a polymer film from the organic electroactive monomer precursor and the biomolecular recognition element, wherein the biomolecular recognition element is entrapped in a spatially uniform manner in the polymer film;
wherein the biomolecular recognition element comprises at least one of a biocatalyst, an inorganic catalyst, an ion-selective material, an antibody, an oligonucleotide, an electrochemical redox mediator, a cell, or an organelle;
wherein the organic electroactive monomer precursor is selected for at least one of its charge rejection properties following conversion to a thin-film of polymer, its anti-biofouling properties following conversion to a thin-film of polymer, its porosity following conversion to a thin-film of polymer, its diffusion-limiting nature following conversion to a thin-film of polymer, or its self-limited growth during conversion to a thin-film of polymer, wherein the organic electroactive monomer precursor is at least one of aniline, pyrrole, acetylene, phenylene, phenylene vinylene, phenylene diamine, thiophene, 3,4-ethylenedioxythiophene, or aminophenylboronic acid.

8. The method of claim 7 wherein the tissue-penetrating electrochemical sensor further comprises a counter electrode.

9. The method of claim 7 wherein said tissue-penetrating electrochemical sensor further comprises a reference electrode.

10. The method of claim 7 wherein the oxidizing potential or reducing potential is either a fixed potential or a time-varying potential.

11. The method of claim 10 wherein the oxidizing potential or reducing potential is applied using one of an amperometric technique, a voltammetric technique, a conductometric technique, or a coulometric technique.

12. The method of claim 10 wherein the oxidizing potential or the reducing potential is selected to result in the formation of a thickness of the conducting polymer film ranging from 5 to 50 nanometers.

13. The method of claim 10 wherein the oxidizing potential or the reducing potential is applied for a specified time duration to result in the formation of a thickness of the conducting polymer film ranging from 5 to 50 nanometers.

14. A method for the fabrication of a tissue-penetrating electrochemical sensor for the quantification of a chemical or biochemical entity in a physiological fluid, the method comprising:
immersing a tissue-penetrating electrochemical sensor comprising a working electrode and at least one additional electrode, in a solution comprising a biomolecular recognition element and an organic electroactive monomer precursor dissolved in the solution;
applying a voltage ranging from −0.2 volt to +1.0 volt from a potentiostat to the working electrode;
electrodepositing on the spatially-defined working electrode a polymer film from the organic electroactive monomer precursor and the biomolecular recognition element, the polymer film having a thickness ranging from 5 to 50 nanometers, wherein the biomolecular recognition element is entrapped in a spatially uniform manner in the polymer film;
wherein the biomolecular recognition element comprises at least one of a biocatalyst, an inorganic catalyst, an ion-selective material, an antibody, an oligonucleotide, an electrochemical redox mediator, a cell, or an organelle;
wherein the organic electroactive monomer precursor is selected for at least one of its charge rejection properties following conversion to a thin-film of polymer, its anti-biofouling properties following conversion to a thin-film of polymer, its porosity following conversion to a thin-film of polymer, its diffusion-limiting nature following conversion to a thin-film of polymer, or its self-limited growth during conversion to a thin-film of polymer.

* * * * *